United States Patent [19]

Supp et al.

[11] 4,271,086
[45] Jun. 2, 1981

[54] PRODUCTION OF METHANOL

[75] Inventors: Emil Supp, Dietzenbach; Heinz Jockel, Klein-Gerau; Gerhard Cornelius, Bergen-Enkheim; Friedmann Marschner, Oberursel, all of Fed. Rep. of Germany

[73] Assignee: Metallgesellschaft Aktiengesellschaft, Frankfurt am Main, Fed. Rep. of Germany

[21] Appl. No.: 35,964

[22] Filed: May 4, 1979

Related U.S. Application Data

[63] Continuation of Ser. No. 856,565, Dec. 1, 1977, abandoned, which is a continuation of Ser. No. 724,032, Sep. 17, 1976, abandoned.

[30] Foreign Application Priority Data

Jan. 29, 1976 [DE] Fed. Rep. of Germany ....... 2603291

[51] Int. Cl.³ .................... C07C 29/15; C07C 27/06; C07C 31/04
[52] U.S. Cl. .................................................. 518/704
[58] Field of Search ...................... 260/449.5; 252/373

[56] References Cited

U.S. PATENT DOCUMENTS

| | | |
|---|---|---|
| 2,904,575 | 9/1959 | Peet . |
| 3,713,784 | 1/1973 | Hess et al. . |
| 3,763,205 | 10/1973 | Green . |
| 3,920,717 | 11/1975 | Marion . |

FOREIGN PATENT DOCUMENTS

| | | |
|---|---|---|
| 1,580,390 | 6/1969 | France . |
| 1159035 | 7/1969 | United Kingdom . |
| 1190071 | 4/1970 | United Kingdom . |
| 1262479 | 2/1972 | United Kingdom . |
| 1316705 | 5/1973 | United Kingdom . |

*Primary Examiner*—Howard T. Mars
*Attorney, Agent, or Firm*—Sprung, Felfe, Horn, Lynch & Kramer

[57] ABSTRACT

In the production of methanol from gaseous hydrocarbons having a lower C/H ratio than is stoichiometrically required to produce methanol and comprising the steps of catalytically cracking said hydrocarbons in the presence of water vapor at about 830° to 930° C. and about 5 to 30 bars to produce a synthesis gas consisting essentially of hydrogen and oxides of carbon, and subsequently catalytically converting said synthesis gas of hydrogen and oxides of carbon to methanol at about 230° to 280° C. and about 30 to 150 bars, the improvement which comprises transferring heat from the hot synthesis gas to the hydrocarbon-water vapor mixture flowing through the cracking catalyst thereby providing at least part of the heat required for the catalytic cracking of the hydrocarbons and reducing the consumption of thermal-/energy per unit of methanol produced. Advantageously, heat transfer is effected by passing the hot synthesis gas through a convoluted or corrugated tube embedded in the hydrocarbon cracking catalyst. Gaseous carbon-containing constituents of the methanol synthesis exhaust gas are removed by adsorption, and desorption; $CO_2$ may later be removed from the residual methanol synthesis exhaust gas by methanol scrubbing and subsequent stripping, both the desorbed constituents and the $CO_2$ being mixed with the hydrocarbons before they are cracked, whereby the C/H ratio of the hydrocarbon feed is raised and the consumption of the thermal-/energy per unit of methanol produced is reduced.

2 Claims, 1 Drawing Figure

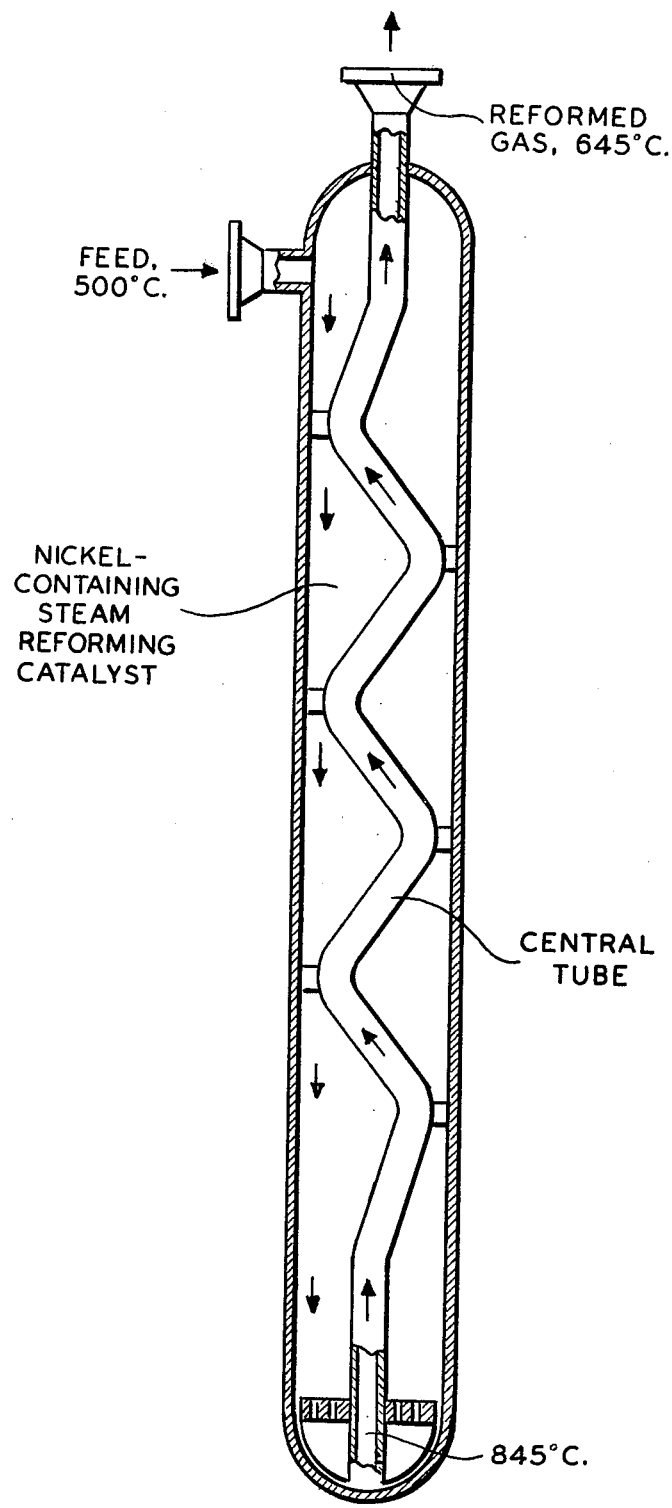

PRODUCTION OF METHANOL

This is a continuation of application Ser. No. 856,565 filed Dec. 1, 1977 now abandoned, which in turn is a continuation of Ser. No. 724,032 filed Sept. 17, 1976, now abandoned.

BACKGROUND

This invention relates to a process of producing methanol from gaseous hydrocarbons having a lower C/H ratio than is stoichiometrically required to produce methanol, comprising catalytically cracking said hydrocarbons in the presence of water vapor at 830° to 930° C. and 5 to 30 bars to produce a synthesis gas which consists essentially of hydrogen and oxides od carbon, and subsequently effecting a catalytic reaction of hydrogen with oxides of carbon at 230° to 280° C. and 30 to 150 bars.

It is known that methanol can be produced by a process in which light hydrocarbons in contact with a nickel-containing catalyst are cracked at 800° to 900° C. and pressures between 1 bar and about 30 bars in the presence of water vapor to produce a synthesis gas which consists essentially of hydrogen, oxides of carbon, and residual methane and which is cooled with condensation of the residual water vapor and is then compressed to pressures of 40 to 120 bars and contacted with a catalyst that consists substantially of copper at temperatures of 230° to 280° C. whereby methanol is formed from hydrogen and part of the oxides of carbon (H. Hiller, F. Marschner, E. Supp, The LURGI-Low Pressure Methanol-Process, CEEF (Tokyo); chem. Economy and Engineer Review, September 1971).

Methanol can also be produced from a synthesis gas which has been produced by the cracking of hydrocarbons in contact with an indirectly heated, nickel-containing catalyst at temperatures above 700° C. in the presence of water vapor. To produce methanol from said synthesis gas, the latter is contacted at 230° to 280° C. and 30 to 80 kg/cm$^2$ with a copper-containing catalyst contained in tubes which are indirectly cooled with water. It is known that the heat generated by the methanol-producing reaction can be utilized by extracting it from the reactor tubes and using it to produce high-pressure steam.

At least part of the high-pressure steam thus produced may be expanded against a back pressure of 4 to 6 kg/cm$^2$ with performance of work and the resulting low-pressure steam may be used as a heat source for the final distillation or the resulting high-pressure steam may be expanded to ambient pressure in condensing turbines (German Pat. Specification No. 2,013,297-U.S. Pat. No. 3,713,784).

In a process in which the heat generated by the methanol-producing reaction is not used to produce water vapor, the waste heat from the tubular heater, i.e., the difference between the supplied heat and the heat required to heat the natural gas-water vapor mixture from the inlet temperature to the reaction temperature and for the endothermic cracking reaction, plus the heat content of the hot cracked gas, is not sufficient to meet the heat and power requirements involved in the production of methanol so that additional fuel must be burnt. On the other Hand, those processes in which the heat generated by the synthesis of methanol is utilized to produce water vapor result in a certain heat and energy surplus, which is not utilized in the process itself because the water vapor produced by the heat of reaction is at a lower temperature than the tubular heater for this reason cannot be used to supply heat to the tubular heater so as to reduce the fuel consumption.

Where natural gas is used as a feedstock, the known processes in which the heat generated by the methanol-producing reaction is not utilized or is utilized only in part involve a heat consumption of $8.1 \times 10^6$ to $8.4 \times 10^6$ kcal per ton of pure methanol product.

In processes in which the heat of reaction is virtually completely utilized to produce water vapor, the heat consumption is $7.8 \times 10^6$ to $7.9 \times 10^6$ kcal.

It is an object of the invention to further reduce the heat consumption per ton of pure methanol produced, also to provide an optimized and more economical methanol synthesis process, and to reduce the capital requirement.

This object is accomplished according to the invention in that part of the heat required for the catalytic cracking of the hydrocarbons is transferred from the hot synthesis gas to the hydrocarbon-water vapor mixture flowing through the cracking catalyst whereby the consumption of thermal-/energy per unit of methanol product is reduced.

The heat is suitably transferred in a temperature range between a synthesis gas end temperature of at most 930° C. and a hydrocarbon-water vapor mixture inlet temperature of at least 400° C.

According to a preferred further feature of the invention, $CO_2$ is scrubbed from the methanol synthesis exhaust gas and separated from the used scrubbing liquor and admixed with the hydrocarbons before they are cracked, whereby the C/H ratio is improved and the consumption of thermal-/energy per unit of methanol product is reduced.

According to another preferred feature of the process according to the invention, carbon-containing gaseous constituents are adsorbed from the methanol synthesis exhaust gas and admixed with the hydrocarbons before the latter are cracked, so that the consumption of thermal-/energy per unit of methanol product is reduced.

According to a further preferred feature of the invention, methanol is used to scrub $CO_2$ from the methanol synthesis exhaust gas.

Within the scope of the invention, the hot synthesis gas is conducted through a convoluted or corrugated tube, which is embedded in the cracking catalyst to transfer heat from the hot synthesis gas to the hydrocarbon-water vapor mixture. A suitable tube element for the furnace is shown in U.S. Pat. No. 3,713,734.

The advantages afforded by the invention reside particularly in a considerable reduction of the heat consumption per ton of pure methanol. The process according to the invention operates in an optimum manner and is highly economical. The capital requirement for a methanol synthesis plant has been much reduced.

The use of the process according to the invention has reduced, the heat requirement per ton of methanol product from the best values known at present and amounting to about 7.85 million kcal/ton to values as low as 7.2 million kcal/ton for example.

In the process, part of the heat content of the hot cracked gases leaving the reaction zone is transferred by means of a tube centrally disposed in the cracking tube to the mixed feedstocks flowing through the catalyst so that the fuel requirement of the tubular heater is much reduced.

Because the cracked gas outlet temperature is lowered from the previous value of 865° C. to about 650° C., the selection of materials for outlet pigtails, outlet manifolds and succeeding high-pressure waste heat boilers is much simplified.

In processes involving the use of light and gaseous hydrocarbon feedstocks, such as natural gas having a C-number of 1.17 and a lower calorific value of 9543 kcal/standard $m^3$ corresponding to 1015 BTU/SCF, the supply of heat was previously determined by the fuel requirement of the tubular heater and the resulting waste heat content of the flue gas and cracked gas and the steam produced in the synthesizer. Because the heat requirement of the tubular heater could not be decreased, a small part of the supplied energy had to be carried off as steam or as electric energy. The novel system involves a reduced fuel requirement of the tubular heater and enables a virtually perfect energy balance to be achieved in the production of methanol.

The drawing schematically shows a suitable apparatus for effecting catalytic cracking and heat exchange of the product.

The invention will be explained more fully in the following examples.

EXAMPLE 1

798.7 standard $m^3$ natural gas having the following composition in mole percent:
$CO_2$—1.60
$N_2$—0.52
$CH_4$—85.93
$C_2H_6$—8.07
$C_3H_8$—2.72
$iC_4H_{10}$—0.30
$nC_4H_{10}$—0.59
$iC_5H_{12}$—0.11
$nC_5H_{12}$—0.10
$C_6$ hydrocarbons—0.06 together with 1.721 kg water vapor and 80 standard $m^3$ purge gas obtained from the methanol synthesizer and having the following composition in mole percent:
$CO_2$—4.49
$CO$—3.25
$H_2$—79.25
$CH_4$—12.13
$N_2$—0.39
$H_2O$—0.02
$CH_3OH$—0.47
are fed at 500° C. to a nickel-containing catalyst contained in tubes and are heated there at 15 bars to 865° C. by a supply of extraneous heat and are thus cracked to produce 3.463 standard $m^3$ synthesis gas having the following composition in mole percent:
$CO_2$—6.49
$CO$—16.92
$H_2$—72.37
$CH_4$—4.10
$N_2$—0.13
and containing also 918 kg water vapor which has not been decomposed. The hot synthesis gas is cooled with condensation of the residual water vapor. The heat which is thus extracted is dissipated as follows:
  869,000 kcal are used to produce 1,877 kg water vapor at 112 bars from feed water supplied at 250° C.
  179,300 kcal are used to preheat the mixture of 798.7 standard $m^3$ natural gas and 80 standard $m^3$ purge gas from 25° to 400° C.
  374,300 kcal are used to heat 3670 kg feed water from 105° to 207° C.
  120,700 kcal are used to heat 2514 kg fresh water and condensates from 42° to 90° C.
  The remaining heat amounting to 260,000 kcal is dissipated in part to cooling air and in part to cooling water.

The residual steam condensed from the synthesis gas contains 50,000 kcal as it is separated from the synthesis gas.

The cooled synthesis gas is compressed in a turbocompressor from 13.5 bars to 61 bars and mixed with 12,044 standard $m^3$ unreacted recycle gas. The resulting mixture is heated to about 230° C. and fed to a copper-containing catalyst, which is contained in tubes. In contact with said catalyst, part of the oxides of carbon react with hydrogen to produce 1000 kg methanol, 134 kg water and about 1.5 kg dimethyl ether, methyl formate, hydrocarbons, higher alcohols and traces of other organic compounds. To control the exothermic reaction, the catalyst-filled tubes are surrounded with boiling water at 40 bars. The mixture of methanol, water, and unreacted synthesis and recycle gases leaving the catalyst is at a constant temperature of 256° C. This mixture is further cooled to about 35° C. in order to condense the methanol which has been formed and other condensible constituents. For this purpose the mixture is conducted in a countercurrent to the mixed synthesis and recycle gases flowing to the reactor which contains the catalyst-filled tubes, and is subsequently cooled with air and water. 14.6 standard cubic meters dissolved gas having the following composition in mole percent:
$CO_2$—37.26
$CO$—3.64
$H_2$—35.28
$CH_4$—23.51
$N_2$—0.31
remain dissolved in the condensate as it is removed and are fed with the latter to the methanol distillation unit, in which the dissolved gas is released by being partly flashed and partly stripped from the methanol together with the constituents having a lower boiling point than methanol.

1188 kg water vapor are produced from the boiling water in the reactor and are withdrawn from the latter under a pressure of 40 bars. Feed water is supplied at 207° C.

To keep the inert gas content of the recycle gas within certain limits, 1.123 standard $m^3$ purge gas having the above-mentioned composition are branched from the recycle gas. The remaining recycle gas is at 57 bars and is compressed to 61 bars in a turbo-compressor and is then admixed with the fresh synthesis gas. The fuel burnt to heat the cracking tubes contained in the tubular heater and filled with nickel-containing catalyst consists mainly of purge gas—after the removal therefrom of 80 standard $m^3$, which are added to the natural gas—and the dissolved and released gas and low-boiling constituents from the methanol distillation unit. These have a total calorific value of 3,410,000 kcal. In addition thereto, 28.8 standard $m^3$ natural gas having a calorific value of 274,900 kcal are burnt. 4000 standard cubic meters of combustion air are required and are preheated to 330° C. 2,334,000 kcal of the heat content of the flue gases produced by the combustion are used in part for heating the natural gas-water mixture flowing through the cracking tubes, in part for the cracking reaction and in part to compensate for the heat losses of the tubular heater. 4748 standard m³ flue gas having the following composition in mole percent:

$CO_2$—5.2
$O_2$—2.1
$N_2$—68.2
$H_2O$—24.5 leave the tubular heater at 980° C. and are cooled in the following manner before being discharged at 150° C. through the flue gas chimney into the atmosphere.

265,500 kcal are used to heat the natural gas-water vapor mixture from about 400° C. to 500° C.
493,200 kcal are used to superheat at 2316 kg steam at 118 bars to 500° C. and to heat 1,188 kg steam at 40 bars to 420° C.
183,000 kcal are used to produce 439 kg steam at 112 bars from feed water at 250° C.
189,000 kcal are used to heat 3670 feed water from 207° C. to 250° C.
420,000 kcal are used to heat 4000 standard m³ combustion air from 25° C. to 330° C.

The total heat quantity to be dissipated from the synthesis gas from its discharge from the tubular heater until it has been cooled to 35° C. and from the flue gas until it has been cooled to 150° C. amounts to 3,413,300 kcal.

Water vapor is available in the following quantities:
2316 kg at 490° C. and 108 bars;
1188 kg at 420° C. and 37.5 bars.

The steam under the higher pressure is fed to the turbine for driving the synthesis gas compressor and is expanded in a first stage to 22.5 bars with performance of work. 1721 kg steam are then bled from the turbine and admixed as process steam with the natural gas to be cracked. The remaining 595 kg are expanded to a pressure of 0.13 bars and are condensed after having been discharged from the second turbine stage. The work performed by the expanding steam is used to meet the power requirement of the synthesis gas compressor, amounting to 276 kW. The 1188 kg steam which have been heated to 420° C. at 37.5 bars are utilized as follows:

The following quantities are expanded to 5.7 bars: 576 kg in the turbine for driving the synthesis gas compressor, 223 kg in the turbine for driving the feed water pumps, and 150 kg in the first stage of a turbine for driving an electric generator.

The remaining 299 kg are expanded to 0.13 bar in the second stage of the turbine for driving the electric generator and are subsequently condensed.

Of the steam expanded to 5.7 bars, 82 kg are used in part for driving the oil pumps for the compressors with expansion to 0.13 bar and partly for small consumers. The remaining 807 kg, which are still at about 265° C. at 5.7 bars, are quenched to saturated steam temperature with 43 kg feed water at 105° C. 850 kg steam are then available for the distillation of methanol.

The expansion in the turbine with performance of work results in a production of 85 kWh at the terminals of the electric generator. As the small consumers consisting of the flue gas and air blowers, fans for air coolers, condensing pumps, etc., consume 32 kWh, 53 kWh must be carried off.

The heat required per ton of pure methanol amounts to 7,896,830 kcal and is supplied in the form of natural gas.

EXAMPLE 2

As in Example 1, 798.7 standard m³ natural gas having the above-mentioned composition together with 1721 kg water vapor and 80 standard m³ purge gas are fed at 500° C. to tubular heater tubes filled with a nickel-containing steam reforming catalyst and are heated therein to 865° C. and cracked to produce 3463 standard m³ synthesis gas. 918 kg of the water vapor are not decomposed. This example differs from Example 1 in that the synthesis gas and residual vapor are not withdrawn from the cracking tubes at the final reaction temperature of 865° C. but are conducted countercurrent to the natural gas-water vapor mixture through a tube, as described in the accompanying drawing, which is arranged in the catalyst at the center of the cracking tube and transfer part of their sensible heat to said mixture so that the latter is heated. The synthesis gas and residual steam leave the tubes centrally disposed in the cracking tubes at 645° C. and are cooled as follows 372,200 kcal are dissipated to produce 933 kg water vapor at 112 bars from feed water at 258° C.
179,300 kcal are dissipated to preheat the mixture of 798.7 standard m³ natural gas and 80 standard m³ purge gas from 25° C. to 400° C.
273,800 kcal are dissipated to heat 2140 kg feed water from 135° C. to 258° C.
95,500 kcal are dissipated to heat 3189 kg feed water from 105° C. to 135° C.
119,400 kcal are used to preheat 2488 kg fresh water and condensate from 42° C. to 90° C.

The remaining heat amounting to 230,000 kcal is dissipated in part by cooling air and in part by cooling water.

Methanol is produced as in Example 1; only the production of water vapor is different. In this example the feed water fed to the synthesis reactor is at a temperature of only 135° C. and only 1041 water vapor at 40 bars are produced.

To heat the tubular heater which comprises the cracking tubes, 950.3 standard m³ purge gas having a total calorific value of 3,044,700 kcal are burnt with 3297 standard m³ air which have been preheated to 350° C., whereby 3932 standard m³ flue gas are produced, from which 2,010,000 kcal are dissipated to heat the natural gas-water vapor mixture and to compensate for the external heat losses of the tubular heater. The flue gas then leaves the tubular heater at 980° C. Additional 107.8 standard m³ purge gas and the dissolved and released gas and the low-boiling compounds from the distillation unit, having a total calorific value of 365,300 kcal, are burnt in a combustion chamber disposed outside the tubular heater with 403 standard m³ air, which have been preheated to 350° C. The resulting flue gases are mixed with those from the tubular heater. The hot flue gases are cooled as follows:

471,600 kcal are dissipated to produce 1207 kg steam at 112 bars from feed water at 258° C.
333,800 kcal are dissipated to superheat 2140 kg steam at 112 bars from saturated steam temperature to 500° C.
269,800 kcal are used to heat the mixture of 798.7 standard m³ natural gas and 80 standard m³ purge gas from 400° C. and 1721 kg water vapor from 275° C. to 500° C.
333,800 kcal are used to superheat 807 kg steam at 40 bars to 450° C.

388,500 kcal are used to heat 3700 standard m³ air to 350° C.

The total heat quantity to be dissipated from the synthesis gas from its discharge from the tubular heater until it has been cooled to 35° C. and from the flue gas until it has been cooled to 150° C. amounts to 3,067,100 kcal.

Water vapor is available in the following quantities:
2140 kg at 500° C. and 108 bars;
807 kg at 450° C. and 38 bars;
234 kg at saturated steam temperature and 40 bars.

1917 kg steam at 500° C. and 108 bars are fed to the turbine for driving the synthesis gas compressor. 1487 kg are bled from the turbine at 290° C. and 22.5 bars and mixed with 234 kg saturated steam at 40 bars. The mixture is conducted as process steam together with the natural gas over the cracking catalyst. 430 mg are expanded to 0.12 bars in a second turbine stage and are condensed after having left the turbine. The remaining 223 kg of the steam at 108 bars are expanded to 0.12 bars in the turbine for driving an electric generator to produce 55 kWh of electric energy, and are then condensed. All steam at 450° C. and 38 bars is expanded to 5.6 bars in turbines for driving the recycle gas compressor, the oil pumps for the compressor, the feed pumps, and the flue gas and air blowers. 807 kg steam leave the turbines and are jointly quenched with 60 kg feed water at 105° C. to produce 867 kg saturated steam. 850 kg are required for the methanol distillation unit and 17 kg for small consumers. The small consumers of electrical energy, consisting of the condensate pumps, fans for air coolers, etc., have a total requirement of 16 kWh so that 39 kWh must be carried off.

The heat required per ton of pure methanol amounts to 7,621,995 kcal and is supplied in the form of natural gas.

EXAMPLE 3

746.2 standard m³ natural gas having the composition stated in Example 1 together with 1610 kg water vapor and 59.4 standard m³ of a $CO_2$ gas which has been separated from the purge gas from the methanol synthesizer and has the following composition in mole percent:
$CO_2$—78.45
CO—1.63
$H_2$—14.19
$CH_4$—5.73
are fed at 500° C. to a nickel-containing cracking catalyst and are heated to 865° C. and cracked at 15 bars to produce 3192 standard m³ synthesis gas having the following composition in mole percent:
$CO_2$—7.25
CO—17.82
$H_2$—70.87
$CH_4$—3.84
$N_2$—0.12
and containing 881 kg water vapor which has not been decomposed. As described in Example 2, the hot synthesis gas dissipates part of its heat to the natural gas-water vapor-$CO_2$ mixture flowing through the catalyst and is at a temperature of 645° C. as it leaves the tubular heater which contains the cracking tubes.

Additional heat is dissipated as follows:
329,500 kcal are used to produce 895 kg water vapor at 112 bars from feed water supplied at 270° C.
161,000 kcal are used to preheat 746.2 standard m³ natural gas and 59.4 standard m³ $CO_2$ gas from 25° C. to 400° C.
254,400 kcal are used to heat 1739 kg feed water from 134° C. to 270° C.
85,000 kcal are used to heat 2829 kg feed water from 105° C. to 134° C.
102,000 kcal are used to preheat 2040 kg fresh water and condensate from 40° C. to 90° C.
456,200 kcal are dissipated in part by cooling air and in part by cooling water.

The synthesis gas entering the synthesis gas compressor is at 35° C. and 13.5 bars.

The synthesis gas is mixed with 11,173 standard m³ unreacted recycle gas. The mixed gases are heated to 230° C. and fed to the above mentioned, copper-containing catalyst. In contact with the latter, part of the oxides of carbon react with hydrogen to produce 1000 kg methanol, 138 kg water, and 1.5 kg other products. The heat of reaction is virtually completely dissipated to the boiling water which surrounds the tubes that contain the catalyst. In this way, 1090 water vapor at 40 bars are produced from feed water supplied at 134° C. The unreacted recycle gas is cooled as described in Example 1, and the methanol, water and the other condensible constituents which have lower and higher boiling points than methanol are liquefied and separated from the recycle gas. 17.4 standard m³ of a gas having the following composition in mole percent:
$CO_2$—43.05
CO—3.35
$H_2$—29.57
$CH_4$—23.72
$N_2$—0.31
remain dissolved in the liquid and are subsequently released in the methanol distillation unit from the methanol together with the low-boiling constituents. When the methanol has been separated, 850.7 standard m³ purge gas having the following composition in mole percent:
$CO_2$—5.66
CO—3.46
$H_2$—76.35
$CH_4$—13.70
$N_2$—0.44
$H_2O$—0.02
$CH_3OH$—0.37
are branched from the recycle gas and are cooled to −30° C. in a heat exchanger and then fed at 56 bars to a scrubbing column, in which the purge gas is scrubbed with methanol at −36° C. in a countercurrent. In addition to the previous gas content of the methanol scrubbing fluid, the latter absorbs 59.5 standard m³ of a gas having the following composition in mole percent:
$CO_2$—78.45
CO—1.63
$H_2$—14.19
$CH_4$—5.73
In a second column, this "$CO_2$ gas" is recovered from the methanol in that the latter is flashed at −36° C. to 0.35 bar and together with natural gas and water vapor is supplied to the synthesizer. The thus regenerated methanol is then used as a scrubbing fluid in the first absorption column. 787.9 standard m³ unabsorbed residual purge gas having the following composition in mole percent:
$CO_2$—0.19
CO—3.61
$H_2$—81.37
$CH_4$—14.36
$N_2$—0.47 leave the scrubbing column at −35° C. and are first warmed to 3° C. in a countercurrent to the gas entering the scrubbing column and are subsequently expanded in a turbine to 10 kg/cm² (absolute pressure) with performance of work and thus cooled to about −79° C. 23.4 kWh are taken from an electric generator driven by the turbine. The gas leaving the turbine is warmed to −35° C. in a countercurrent to the gas which enters the scrubbing column and which is thus cooled to −30° C. The thus warmed gas is used in the methanol distilling unit to condense the pure methanol, whereby the gas is warmed to 12° C. The gas is then burnt as fuel in the tubular heater.

Heat is supplied to the tubular heater in that 787.9 standard m³ residual purge gas, 17.4 standard m³ dissolved and released gas, the low-boiling constituents which become available in the distillation unit, and 15.4 standard m³ natural gas, having a total calorific value of 2,875,800 kcal, are burnt with 3343 standard m³ air at 350° C. 3909 standard m³ flue gases are produced, which transfer 1,856,000 kcal for heating the mixture of natural gas, $CO_2$ gas and water vapor to 865° C., for the endothermic cracking reaction and to compensate the heat losses of the tubular heater and leave the same at 980° C. In the flue gas duct, additional 10.7 standard m³ natural gas are burnt with 124 standard m³ air to produce 138 standard m³ flue gas, which are mixed with the flue gas leaving the cracking heater. 4047 standard m³ flue gas having a heat content of 1,507,200 are then available.

The flue gases are cooled as follows:
- 316,500 kcal are used to produce 843 kg water vapor at 112 bars from feed water at 270° C.
- 243,100 kcal are used to heat the natural gas-$CO_2$ gas mixture from 400° C. and 1610 kg water vapor from 288° C. to 500° C.
- 276,700 kg are used to superheat 1739 kg steam at 112 bars to 500° C.
- 104,600 kcal are used to superheat 807 kg steam at 40 bars to 450° C.
- 364,000 kcal are used to heat the combustion air from ambient temperature to 350° C.
- 202,300 are lost through the chimney with the flue gas at 150° C.

The total heat quantity to be dissipated from the synthesis gas from its discharge from the tubular heater until it has been cooled to 35° C. and from the flue gas until it has been cooled to 150° C. amounts to 2,693,000 kcal.

Water vapor is available in the following quantities:
1739 kg at 500° C. and 108 bars;
807 kg at 450° C. and 38 bars;
283 kg saturated steam at 40 bars.
The steam at 500° C. and 108 bars is fed to a turbine for driving the synthesis gas compressor to 22.5 bars and are thus caused to assume a temperature of 290° C. and are then mixed with the 283 kg saturated steam at 40 bars. The mixture is fed as process steam to the cracking step. The remaining 412 kg steam at 108 bars are expanded to 0.12 bars in a second turbine stage and subsequently condensed. 807 kg steam at 450° C. and 38 bars are expanded to 5.6 bars in the turbines for driving the recycle gas compressor, the feed pumps, the oil pumps for the compressors, and the flue gas and air blowers and supply the power required to drive these machines. The exhaust steam becomes available at 260° C. and 5.6 bars and is quenched with 60 kg feed water at 100° C. whereby 867 kg saturated steam are produced. 850 kg of said saturated steam are used in the methanol distillation unit and 17 kg for small consumers.

The energy consumption of the small consumers, inclusive of the compressor for compressing 59.5 standard m³ $CO_2$ gas from 0.3 bar to 23 bars, amounts to 23 kWh, which are supplied by the expansion of the residual purge gas in the turbines.

The heat required per ton of pure methanol amounts to 7,369,600 kcal and is supplied in the form of natural gas.

EXAMPLE 4

658.4 standard m³ natural gas having the same composition as in Example 1 are mixed with 257.6 standard m³ of mixed gases separated from the purge of the synthesis—these mixed gases will be referred to as C fraction hereinafter—and having the following composition in mole percent:
$CO_2$—15.29
CO—10.95
$H_2$—21.35
$CH_4$—50.31
$N_2$—2.10
and with 14 standard m³ dissolved and released gas obtained from the methanol distillation unit and having the following composition in mole percent:
$CO_2$—40.71
CO—3.57
$H_2$—26.43
$CH_4$—28.57
$N_2$—0.72
and with 1421 kg water vapor. The mixture is cracked as described in Example 2 to produce 3244 standard m³ synthesis gas having the following composition in mole percent:
$CO_2$—6.23
CO—18.67
$H_2$—69.66
$CH_4$—5.23
$N_2$—0.21
and containing 721 kg residual water vapor. The final reaction temperature is 865° C. The hot synthesis gas transfers 328,900 kcal to the mixture of natural gas, water vapor etc. flowing through the nickel catalyst and is at 645° C. as it leaves the tubular heater. The synthesis gas is cooled as follows:
- 323,500 kcal are used to produce 949 kg steam at 112 bars.
- 164,600 kcal are used to preheat 658.4 standard m³ natural gas, 257.6 standard m³ C fraction and 14 standard m³ dissolved and released gas from ambient temperature to 400° C.
- 300,900 kcal are used to heat 1628 kg feed water from 129° C. to 297° C.
- 65,500 kcal are used to heat 2724 kg feed water from 105° C. to 129° C.
- 83,800 kcal are used to preheat 1709 kg fresh water and condensate from 41° C. to 90° C.
- 314,900 kcal are dissipated in part by cooling air and in part by cooling water.
- 63,000 kcal are discharged with the condensate recovered from the gas.

The synthesis gas is at 35° C. and 13.5 bars as it enters the synthesis gas compressor.

The synthesis gas is mixed with 11,354 standard m³ recycle gas. The mixture is heated to 230° C. and conducted in contact with the copper catalyst contained in tubes, whereby 1000 kg methanol, 114 kg water, and 1.5 kg of the by-products mentioned in Example 1 are formed. 1096 kg water vapor at 40 bars are produced as the heat of reaction is dissipated to the boiling water which surrounds the catalyst tubes. Feed water is supplied at 129° C. When the unreacted recycle gas has been cooled and the products formed have condensed, 930 standard m³ purge gas having the following composition in mole percent:

$CO_2$—5.30
CO—3.79
$H_2$—72.35
$CH_4$—17.42
$N_2$—0.74
$H_2O$—0.02
$CH_3OH$—0.38 are withdrawn from the cycle. 18 standard m³ gas having the following composition in mole percent:

$CO_2$—40.74
CO—3.49
$H_2$—26.63
$CH_4$—28.65
$N_2$—0.49 are dissolved in the liquid product and 14 standard m³ of said dissolved gas are released as the methanol is flashed to 5 bars. The remaining 4 standard m³ are recovered together with the low-boiling constituents in the methanol distillation unit.

190 standard m³ purge gas are branched from the 930 standard m³, whereas 740 standard m³ are fed to a pressure swing adsorption plant, in which 482.4 standard m³ hydrogen are separated in known manner and are mixed with the previously branched off 190 standard m³ purge gas. The resulting mixture is heated to 220° C. in a countercurrent to the recycle gas leaving the synthesis reactor and is then expanded from 55 bars to 2 bars in a turbine and leaves the same at 17° C. An electric generator coupled to the turbine delivers 54.2 kWh. The hydrogen is available as fuel for the tubular heater.

The C fraction consisting of the gas that has been adsorbed from the purge gas and desorbed by a pressure relief and amounting to 257.6 standard m³ and having the composition described above together with the 14 standard m³ dissolved and flashed-off gas is compressed from the desorption pressure of 1.03 bars to 21 kg/cm² (absolute pressure). The compressed mixture is admixed with the process natural gas.

The fuel used to heat the tubular heater which contains the cracking tubes consists of a mixture of 482.4 standard m³ hydrogen, 190 standard m³ purge gas, 4 standard m³ dissolved and released gas and the low-boiling compounds from the methanol distillation unit, and 92.6 standard m³ natural gas and has a total heat content of 2,860,000 and is burnt with 3214 standard m³ air at 350° C. to produce 3755 standard m³ flue gas. 1,823,400 kcal are used to heat the gas-vapor mixture flowing through the catalyst, for the endothermic cracking reaction, and to compensate for the heat losses of the tubular heater. The flue gas is at 980° C. as it leaves the tubular heater.

Cooling is effected as follows:
231,400 kcal are used to produce 679 kg steam at 112 bars from feed water at 297° C.
195,400 kcal are used to superheat the mixture of natural gas, C fraction, and water vapor to 500° C.
259,200 kcal are used to superheat 1628 kg steam at 112 bars to 500° C.
105,000 kcal are used to superheat 810 kg steam at 40 bars to 450° C.
332,000 kcal are used to heat 3214 standard m³ air from ambient temperature to 350° C.
187,800 kcal are carried by the flue gas at 150° C. into the atmosphere.
The total heat quantity dissipated from the synthesis gas from its discharge from the tubular heater until it has been cooled to 35° C. and from the flue gas until it has been cooled to 150° C. amounts to 2,440,200 kcal.

Water vapor is available in the following quantities:
1628 kg at 500° C. and 108 bars;
810 kg at 450° C. and 38 bars;
266 kg saturated steam at 40 bars.

1135 kg of the steam at 108 bars are expanded to 22.5 bars in the first stage of the turbine for driving the synthesis gas compressor and are thus caused to assume a temperature of 290° C. The expanded steam is mixed with the 266 kg saturated steam at 40 bars and the mixture is used as process steam. 493 kg are expanded to 0.12 bar in the second turbine stage and subsequently condensed. The turbine produces 258.5 kWh. 810 kg steam at 450° C. and 38 bars are expanded to 5.6 bars in the turbines for driving the recycle gas compressor, the feed pumps, the oil pumps for the compressors and the flue gas and air blowers and thus produce energy for driving these machines.

The exhaust steam at 260° C. is quenched to saturated steam temperature with 60 kg feed water at 105° C. to produce 870 kg saturated steam. 850 kg of the latter are consumed by the methanol distillation unit and 20 kg by small consumers. The energy requirement of the small consumers amounts to 15.5 kWh and that of the compressor for the C fraction and dissolved and flashed-off gas amounts to 38.7 kWh. The electric generator driven by the turbine in which the hydrogen-purge gas mixture is expanded delivers 54.2 kWh. It will be understood that the C fraction compressor may also be directly coupled to the expansion turbine if an electric generator is coupled to the other shaft end of said turbine. In this case said generator must deliver only 15.5 kWh to meet the energy requirement of the remaining small consumers.

The heat required per ton of pure methanol amounts to 7,167,270 kcal.

It will be appreciated that the instant specification and examples are set forth by way of illustration and not limitation, and that various modifications and changes may be made without departing from the spirit and scope of the present invention.

What is claimed is:

1. In the production of methanol from gaseous hydrocarbons having a lower C/H ratio than is stoichiometrically required to produce methanol the improvement comprising the steps of:
 (a) mixing said hydrocarbons with water vapor and a carbon dioxide containing gas, the mixture being at a temperature of an inlet temperature of at least about 400° C.,
 (b) feeding said mixture into a tubular reaction zone and catalytically reacting the mixture therein at about 830° to 930° C. and about 5 to 30 bars to produce a synthesis gas consisting essentially of hydrogen and oxides of carbon, said mixture being heated while being catalytically reacted,
 (c) transferring heat from the hot syntheses gas to said mixture by withdrawing the synthesis gas through a convoluted or corrugated tube within the catalyst of each tubular member of said reaction zone in countercurrent and with indirect heat exchange to said mixture, (d) cooling said synthesis gas and withdrawing condensate therefrom, (e) catalytically converting said synthesis gas in a methanol synthesis zone at about 230° to 280° C. and about 30 to 150 bars, (f) separating methanol from the product of said synthesis zone and withdrawing an exhaust gas, from said synthesis zone, said exhaust gas containing hydrogen, carbon dioxide and methane, (g) thereafter adsorbing from said exhaust gas the carbon containing gaseous constituents, desorbing said constituents and mixing them with the hydrocarbons in step (a) before the latter are cracked, scrubbing the residual methanol synthesis exhaust gas with scrubbing liquor to dissolve the carbon dioxide, separating the carbon dioxide from the used scrubbing liquor and mixing it with the hydrocarbons in step (a) before they are cracked and (h) the heat consumption per 1000 kg of pure methanol being in the range of 7.16 to 7.62 million kcal.

2. A process according to claim 1, wherein the scrubbing liquor comprises methanol.

* * * * *

UNITED STATES PATENT AND TRADEMARK OFFICE
CERTIFICATE OF CORRECTION

PATENT NO. : 4,271,086
DATED : June 2, 1981
INVENTOR(S) : Emil Supp et al.

It is certified that error appears in the above—identified patent and that said Letters Patent is hereby corrected as shown below:

Column 1, line 33, before "(Tokyo)" delete "CEEF" and insert -- CEER --.

Column 7, line 54, delete "$H_2$——70.87" and insert

-- $H_2$——70.97 --.

Signed and Sealed this

Twentieth Day of July 1982

[SEAL]

Attest:

GERALD J. MOSSINGHOFF

Attesting Officer

Commissioner of Patents and Trademarks